(12) United States Patent
Davidson et al.

(10) Patent No.: US 7,220,731 B2
(45) Date of Patent: May 22, 2007

(54) DERIVATISED CARBOHYDRATES AND THEIR USE IN SOLID DELIVERY SYSTEMS

(75) Inventors: Iain Davidson, Nottingham (GB); Julian Blair, Nottingham (GB)

(73) Assignee: Elan Drug Delivery Limited (GB)

( * ) Notice: Subject to any disclaimer, the term of this patent is extended or adjusted under 35 U.S.C. 154(b) by 647 days.

(21) Appl. No.: 10/415,549

(22) PCT Filed: Oct. 31, 2001

(86) PCT No.: PCT/GB01/04832

§ 371 (c)(1),
(2), (4) Date: Jul. 24, 2003

(87) PCT Pub. No.: WO02/36600

PCT Pub. Date: May 10, 2002

(65) Prior Publication Data

US 2004/0044196 A1    Mar. 4, 2004

(30) Foreign Application Priority Data

Oct. 31, 2000    (GB)    .................................... 0026593

(51) Int. Cl.
*A61K 31/7024*    (2006.01)
*C07H 3/06*    (2006.01)

(52) U.S. Cl. ..................... 514/54; 536/123.1
(58) Field of Classification Search .................. 514/23, 514/25, 53, 54, 61
See application file for complete search history.

(56) References Cited

U.S. PATENT DOCUMENTS 6,290,991 B1 *   9/2001   Roser et al. ................ 424/502
6,586,006 B2 *   7/2003   Raghuvanshi et al. ...... 424/484

FOREIGN PATENT DOCUMENTS

WO    WO 99/33853 A2    7/1999

OTHER PUBLICATIONS

Hatley, R. "Stabilisation and delivery of labile materials by amorphous carbohydrates and their derivatives" (1999) J. Mol. Catalysis B: Enzymatic, vol. 7, pp. 11-19.*

Ajisaka K. and Fujimoto H. "Regioselective Syntheses of Trehalose-Containing Trisaccha-Rides Using Various Glycohydrolases" *Carbohydrate Research*, 1990, pp. 227-234, Elsevier Science Publishers B.V., Amsterdam.

De Nooy, A "Highly Selective Nitroxyl Radical-Mediated Oxidation of Primary Alcohol Groups in Water-Soluble Glucans" *Carbohydrate Research*, 1995, pp. 89-98, vol. 269.

Imata, H. et al. "The Specificity of Association Between Concanavalin A and Oligosaccharide-Branched Cyclodextrins with an Optical Biosensor" *Bioorganic & Medicinal Chemistry Letters*, 1997, pp. 109-112, vol. 7, No. 2, Elsevier Science Ltd., Great Britian.

Koto, S. et al. "α-D-Glucosylation by 6-O-Acetyl-2,3,4-tri-O-benzyl-D-glucopyranose Using Trimethylsilyl Triflate and Pyridine. Synthesis of α-D-Glucosides" Feb. 1996, pp. 411-414, vol. 59.

Kurakake, M. et al., "Transxylosylation of β-Xylosidase from *Aspergillus awamori* K4" *Biosci. Biotech. Biochem.*, 1997, pp. 2010-2014, vol. 61, No. 12.

Kurimoto, M. et al. "Synthesis by an α-Glucosidase of Glycosyltrehaloses with an Isomaltosyl Residue" *Biosci. Biotech. Biochem.*, 1997, pp. 699-703, vol. 61, No. 4.

Ogawa, T and Matsui, M. "A Novel Oxidative Transformation: Oxidative Esterification" *Journal of the American Chemical Society*, Mar. 17, 1976, pp. 1629-1630.

Park, K.H. et al. "Transglycosylation Reactions of *Bacillus Stearothermophilus* Maltogenic Amylase with Acarbose and Various Acceptors" *Carbohydrate Research*, 1998, pp. 235-246, vol. 313.

Szurmai, Z. et al. "Glycosylated Trehalsoe Synthesis of the Oligosaccharides of the glycolipid-type Antigens from *Mycobacterium Smegmatis*" *Carbohydrate Research*, 1987, pp. 313-325.

Ziegler, T. "Synthetic Studies Toward Pyruvate Acetal Containing Saccharides Synthesis of the Carbohydrate Part of the *Mycobacterium Smegmatis* Pentasaccharide Glycolipid and Frangments Thereof for the Preparation of Neoantigens" *J. Org. Chem.*, 1993, pp. 1090-1099, vol. 58.

* cited by examiner

*Primary Examiner*—Shaojia Anna Jiang
*Assistant Examiner*—Eric S. Olson
(74) *Attorney, Agent, or Firm*—Saliwanchik, Lloyd & Saliwanchik

(57) ABSTRACT

In a composition comprising a therapeutic agent and a compound which is a trisaccharide or higher polysaccharide, that compound has the formula $X[-Y-Z]_n$ wherein X and Z are each saccharide molecules in which none, some or all OH groups are derivatised; Y is an ester linkage to an exocyclic C atom in X; and n in an integer.

8 Claims, No Drawings

DERIVATISED CARBOHYDRATES AND THEIR USE IN SOLID DELIVERY SYSTEMS

This application is a National Stage Application of International Application Number PCT/GB01/04832, published, pursuant to PCT Article 21(2).

FIELD OF THE INVENTION

This invention relates to derivatised carbohydrates, compositions comprising them, and methods for their use. The derivatised carbohydrates can be used to form solid delivery systems useful for the dissolution, encapsulation, storage and delivery of a variety of therapeutic and diagnostic molecules.

BACKGROUND OF THE INVENTION

Solid delivery systems are useful in a wide variety of applications such as controlled release of labile molecules, particularly bioactive materials such as organic pharmaceutical compounds, enzymes, vaccines and biological control agents such as pesticides and pheromones.

Drugs and other active agents are frequently administered orally by means of solid dosage forms, such as tablets and capsules. Other oral solid dosage forms include lozenges and other hard candies. Solid dosage forms can also be implanted subcutaneously for drug delivery. Additionally, solid dosage forms are delivered intravenously, or by inhalation to the pulmonary system.

Solid dose delivery of bioactive materials to biological tissues such as mucosal, dermal, ocular, subcutaneous, intradermal and pulmonary offers several advantages over methods such as hypodermic injection and transdermal administration via so-called "patches". Using injection, there may be physical discomfort, and there is a risk of infection using conventional needles and syringes. Many drugs are not suitable for transdermal delivery, nor have transdermal drug release rates for those capable of such delivery been perfected. Additionally, transdermal patches often cause topical reactions, in many instances precluding their long-term use.

A variety of formulations have been provided for administration in aerosolized form to mucosal surfaces, particularly "by-inhalation" (naso-pharyngeal and pulmonary). Compositions for by-inhalation administration generally comprise a liquid formulation of the pharmaceutical agent and a device for delivering the liquid formulation in aerosolized form.

U.S. Pat. No. 5,011,678 describes compositions containing a pharmaceutically active substance, a biocompatible amphiphilic steroid and a biocompatible hydrofluorocarbon propellant. U.S. Pat. No. 5,006,343 describes compositions containing liposomes, a pharmaceutically active substance and an alveolar surfactant protein that enhances transport of the liposomes across a pulmonary surface. U.S. Pat. No. 5,608,647 describes methods for administering controlled amounts of aerosol medication from a valved canister.

One drawback to the use of aerosolized formulations is that maintenance of pharmaceutical agents in aqueous suspensions or solutions can lead to lossofactivity and bioavailability. The loss of activity can be partially prevented by refrigeration, but this limits the utility of these formulations. The use of powdered formulations overcomes many of these drawbacks. The particle size of such powders is 0.5-5 μm, in order to attain deep alveolar deposition in pulmonary delivery. Unfortunately, powders of such particle size tend to absorb water and clump, thus reducing deposition of the powder in the deep alveolar spaces.

WO-A-96/03978 describes powders suitable for use in by-inhalation delivery. The powders are of uniform particle size and can be produced with varying degrees of hydrophobicity to reduce clumping and increase drug release in the surfactant environment of the lung. They may also be useful for ballistic delivery.

WO-A-96/03978 describes solid dose delivery systems which include a vitreous vehicle loaded with a guest substance, and which are capable of releasing the quest substance at a controlled rate. Controlled release is achieved by the use of glass-forming, hydrophobically derivatized carbohydrates as solid vehicles, the derivative group being selected to reduce solubility of the matrix material in aqueous media.

WO-A-99/01463 discloses polysaccharides, in which the saccharide units are linked via glycosidic bonds, and in which at least some of the OH groups are derivatised in the form of an ester or ether.

WO-A-99/33853 discloses derivatised carbohydrates, in which some OH groups are substituted with a branched hydrophobic chain, e.g. via an ester or other linkage. Such carbohydrates may be used to form solid delivery systems, e.g. incorporating a therapeutic agent, and which can be in the form of particles intended for administration by inhalation.

For drug delivery, it is advantageous if solid drug delivery systems can have defined size, shape, density and dissolution rate. It is also advantageous that solid drug delivery systems should be capable of sustained, controlled release of the drug. Further, it is desirable that solid dose delivery systems can be formulated using simple and economical methods.

SUMMARY OF THE INVENTION

Derivatised carbohydrates according to the invention are polysaccharides, in which at least one pair of saccharide units is linked via an ester, amide or other bond.

Either for protection during formation of that bond, or in the product for use, some or all of the OH groups on the saccharide units may be derivatised, e.g. in the forms of esters or ethers. Such compounds have the formula $$X[-Y-Z]_n$$

wherein X and Z are each saccharide molecules in which none, some or all OH groups are derivatised; Y is an ester linkage; and n is an integer (i.e. a whole number, and not zero). Compounds of the invention have at least 3 saccharide units Compounds of the invention are useful in forming solid dosage forms of therapeutic agents, e.g. for the controlled release of such agents. They can be readily prepared, and provide a high glass transition temperature (Tg) without having a particularly high molecular weight. Their properties may vary, and may be usefully controlled.

DESCRIPTION OF THE INVENTION

The "core" saccharide X may be, for example, a monosaccharide, disaccharide or trisaccharide in which none, some or all OH groups are derivatised.

Although it maybe a higher saccharide, the "terminal" saccharide Z is preferably a monosaccharide in which none, some or all of the OH groups are derivatised. Preferred examples include glucuronic acid, gluconic acid and galacturonic acid.

Many saccharides are known, and can be used in this invention as X and/or Z. Examples are glucose, lactose, cellobiose, sucrose, trehalose, raffinose, melezitose and stachyose. Both α and β anomers, and mixtures thereof, may be used.

n is preferably 1 or 2. Especially when n is 2, it is preferred that X is a derivatised symmetrical saccharide such as derivatised trehalose. Particular compounds of this type are trehalose 6:6'-di(β-tetraacetylglucuronate)hexaacetate, trehalose 6:6'-dipentaacetyl-glucuronate)hexaacetate, trehalose 6:6'-di(β-tetraacetylglucuronate)-2,3:2',3'-tetra-isobutyrate-4,4'-diacetate and trehalose 6:6'-di(β-tetraacetylglucuronate)hexapropanoate.

In a derivatised compound of the invention, all or some of the OH groups are replaced. Such derivatisation is described in WO-A-96/03978, WO-A-99/01463 and WO-A-99/33853. The OH groups, other than any OH group that forms part of Y, may be substituted, for example via ester or ether linkages, with a straight or branched hydrocarbon chain, such as a branched hydrocarbon chain having 3-30, preferably 3-20 and more preferably 3-8 C atoms. The carbohydrate may be substituted, for example, by esterification of one or more of the hydroxyl groups on the carbohydrate with an acid such as a fatty acid including a branched hydrocarbon chain. Mixed esters and ethers of acids including a branched hydrocarbon chain may be formed, e.g. isobutyrate, pivalate, 2,2-dimethylbutyrate, 3,3-dimethylbutyrate and 2-ethylbutyrate. Optionally, one or more of the remainder of the hydroxyl groups can be substituted via an ester bond with an acid, to give a group such as acetate, propionate or butyrate.

Derivatised carbohydrates within the scope of the invention further include carbohydrates wherein one or more free hydroxyl groups are derivatised, for example into an amine or sulphur group, to which hydrophobic branched hydrocarbon chains may be attached, for example, via an amide or thiol linkage. The formation of such linkages, and also of ether etc. derivatives as described above, is well known to those of ordinary skill in the art.

Procedures for coupling X and Z, to give a compound of the invention, are also known. This may be done before or after derivatisation. Suitable protecting strategies, including orthogonal protection if necessary, are also known.

Thus, for example, a compound $X^1$—$CH_2OH$ or $X^1$—$CH_2$—$NH_2$ ($X^1$ represents that part of X other than the $CH_2OH$ or $CH_2$—$NH_2$ group, respectively, and in which, if necessary or desired, all OH groups may optionally be protected) is reacted with $Z^1$-OH, $Z^1$-$NH_2$ or $Z^1$-COOH ($Z^1$ represents that part of X other than the OH, NH or COOH group, respectively, and in which, if necessary or desired, all OH groups may optionally be protected), under known, ether-, amide- or ester-forming conditions. If desired or necessary, any group may be activated, e.g. as OMs, OTs, or $N_3$.

The accompanying Scheme 1 illustrates the preparation of a preferred compound of the invention (see also Example 1). Further, illustrative compounds of the invention and their synthesis are shown in Schemes 2 (deprotected) and 3 (partially deprotected).

For Scheme 2, ditrityl trehalose is reacted with benzyl bromide and sodium hydride at room temperature. The resulting ditrityl hexabenzyl trehalose 12 is then detritylated in the usual way with Amberlite resin IR120. The product hexabenzyl trehalose 13 is isolated as an oil; mesylation to 14 provides a sticky solid/syrup. 14 is then treated in the presence of sodium glucuronate 15 in solvent.

Converting the sodium salt of the glucuronate to a tetrabutylammonium salt may increase its solubility in organic media and the nucleophilicity of the glucuronate. To this end, sodium glucuronate is dissolved in DMSO and tetrabutylammonium bromide is added. The dimesyl hexabenzyl trehalose 14 is added in situ.

For Scheme 3, hexabenzyl trehalose 13 and tetraacetyl glucuronic acid are coupled using the DCC/DMAP reaction. The resulting compound 18 is debenzylated via hydrogenation over a palladium catalyst to afford the partially deprotected analogue 4.

Compositions, such as solid delivery systems, comprising a compound of the invention, and other components such as bioactives, carbohydrates, binders, and any other constituents suitable for use in drug delivery are also encompassed by the invention. A wide variety of compositions can be incorporated into a solid delivery system, including diagnostic, therapeutic, prophylactic and other biologically active agents. The compositions can be in a vitreous or crystalline form, or mixtures thereof.

Solid delivery systems including a carbohydrate of the invention may incorporate a substance capable of being released from the system. In a preferred embodiment, the solid delivery system comprises the substituted carbohydrate in the form of a vitreous glass matrix having the substance incorporated therein. Advantageously, drugs and bioactive molecules are thereby provided in a solid, non-hygroscopic, glassy matrix, which undergoes a controlled, surface-led devitrification when immersed in an aqueous environment and subsequently effects a sustained release of drug therein.

Properties of the glass matrix, such as the release rate of the substance, can be modulated by choice of modified carbohydrate, and other incorporated materials. The glass matrix may be modified, for example, by the addition of different glass-formers with known release rates. Other materials can be incorporated into the glass matrix during processing to modify the properties of the final composition, including physiologically acceptable glass-formers such as carboxylate, nitrate, sulfate, bisulfate, and combinations thereof. The delivery systems can further incorporate any other carbohydrate and/or hydrophobic carbohydrate derivative, such as glucose pentaacetate or trehalose octaacetate.

The delivery systems can be in any of a variety of forms including lozenge, tablet, disc, film, suppository, needle, microneedle, microfiber, particle, microparticle, sphere, microsphere, powder or implantable device. A composition of the invention in particulate form may be suitable for pulmonary administration, e.g. having a particle size of less than 10 μm, e.g. 1-5 μm, or larger, e.g. for ballistic delivery or for compression into tablets.

The glass matrices formed from carbohydrates as described herein may be used to stabilize labile bioactive molecules immobilized within the glassy matrix. Preferably, a derivatised carbohydrate of the invention has a high glass transition temperature, e.g. from 10 to 150° C., preferably 50 to 110° C., and is physically stable. The glass matrices formed therefrom have increased hydrophobicity, and thus have many applications as drug delivery vehicles, particularly for administration as sustained or delayed release forms. The derivatised carbohydrates permit solid matrices to be formed therefrom with selected controlled release properties. Without being limited to any theory, it is believed that when the solid amorphous matrix is immersed in aqueous environments, drug release is effected by a controlled devitrification which begins over the surface of the glass particle. As water interacts with the glass, the devitrification front proceeds further into the glass. The remaining crystalline matrix allows the previously entrapped drug to diffuse away into the surrounding environment at a rate dependent on both HDC and drug.

The invention enables the preparation and use of derivatised carbohydrates having glass transition temperatures (Tgs) high enough to form stable glasses to allow the formulation of actives such as drugs. In parallel, the glasses undergo a slow, controlled devitrification when immersed in water. The methods of the invention permit the formulation of drugs in very hydrophobic glassy matrices, which can sustain drug release over long time periods.

Derivatised carbohydrates may also be used to form solid matrices that have a partially or substantially crystalline structure. Additionally, glasses may also be formed which form a partially or substantially crystalline structure over time after incorporation of active.

The Tgs of the compositions encompassed herein are typically less than about 200° C., and preferably between 70° C. and 120° C. The derivatised carbohydrates may be used to form glass matrices, wherein the tendency to crystallize from the melt or with reducing solvent, is low. Mixtures of derivatised carbohydrates also may be used to form the glass matrices. Glasses formed using the derivatised carbohydrates preferably have melt temperatures suitable for the incorporation of substances such as biologically active compounds, without thermal degradation, and have Tgs above ambient temperatures.

Both devitrification of the matrix and the fluidity of the melt at temperatures close to Tg can be controlled by choice of the degree and type of substitution of the carbohydrate, and by the addition of modifiers such as other derivative sugars and certain organic compounds. Suitable derivative sugars and organic compounds are described, for instance, in WO-A-96/03978.

As used herein, ambient temperatures are those of the surrounding environment of any given environment. Typically, ambient temperatures are room temperature which is generally 20-22° C. However, ambient temperature of a "warm room" (for bacteriological growth) can be 37° C. Thus, ambient temperature is readily determined from the context in which it is used and is well understood by those of skill in the art.

The derivatised carbohydrates can be used to form a biodegradable delivery system, optionally with a substance incorporated therein, such as a therapeutic substance. The derivatised carbohydrates are referred to herein as the "vehicle" used to form the delivery system. As used herein, the term "delivery system" refers to any form of the substituted carbohydrate having a substance incorporated therein. Preferably, the delivery system is in the form of a solid matrix having the substance incorporated therein. The matrix advantageously can be designed to have a desired release rate of the substance incorporated therein, by selection of the material forming the matrix, selection of the conditions of forming the matrix, and by the addition of other substances which can modify the rate of release.

The derivatised carbohydrates readily form glasses either from a quenched melt or an evaporated organic solvent. Examples of methods of forming amorphous carbohydrate glass matrices are described in "Pharmaceutical Dosage Forms," Vol. 1 (H. Lieberman and L. Lachman, Eds.) 1982.

The derivatised carbohydrates in purified form and substance or substances to be incorporated can be intimately mixed together in the appropriate molar ratios and melted until clear. Suitable melting conditions include, but are not limited to, melting in open glass flasks at about 30-250° C. for about 1-2 minutes. This results in a fluid melt which can be allowed to slightly cool before dissolving the substance in the melt, if required, and quenching to glass for instance by pouring over a brass plate or into a metal mould for shaped delivery vehicles. The melts may also be quenched by any methods including spray chilling. Melt temperature can be carefully controlled and substances can be incorporated into the derivatised carbohydrates either in the premelted formulation, or stirred into the cooling melt before quenching.

The melts are thermally stable and allow the incorporation of molecules without denaturation, or suspension of core particles without alteration of their physical nature. The glass melts can be used also to coat micron-sized particles. This is particularly important in the formulation of non-hygroscopic powders containing hygroscopic actives, for by-inhalation administration of therapeutic agents. Compositions made by this process are also encompassed by this invention.

Alternatively, solid delivery systems can be formed by evaporation of the derivatised carbohydrates and substance to be incorporated in solution in a solvent or mixture of solvents. The solvent maybe organic or aqueous, e.g. a mixture of water and an organic solvent. Suitable organic solvents include, but are not limited to, dichloromethane, chlorofortn, dimethyl sulfoxide, dimethylformamide, ethyl acetate, acetone and alcohols. The exact nature of the solvent may not be critical, especially if it is completely removed on formation of the delivery system. Preferably, both the substituted carbohydrate and substance to be incorporated are soluble in the solvent. However, the solvent may dissolve the substituted carbohydrate and allow a suspension of the substance to be incorporated in the matrix. In one embodiment, on concentrating the solvent, crystallization of the derivatised carbohydrates does not occur. Instead, an amorphous solid ("glass" or "glass matrix") is produced, which has similar properties to the quenched glass. Alternatively, solid matrices which are partially, substantially or fully crystalline may be formed. Substances can be incorporated easily either in solution or as a particle suspension.

In one embodiment, a solution of the substance to be incorporated containing a sufficient quantity of substituted carbohydrate to form a glass on drying can be dried by any method known in the art, including, but not limited to, freeze-drying, lyophilization, vacuum, spray, belt, air or fluidized-bed drying. Another suitable method of drying, exposing a syrup to a vacuum under ambient temperature, is described in WO-A-96/03978. After formation of a glass-containing, homogeneously distributed substance in solid solution or fine suspension in the glass, the glasses can then be milled and/or micronized to give microparticles of homogeneous defined size.

A preferred active agent for use in the invention, especially for delivery to the lung, is insulin. This is a water-soluble macromolecule. Two illustrative procedures are available, in order to encapsulate such macromolecules into lipophilic OED particles, substantially without losing activity, during or post-processing.

One procedure may be described as the single emulsion spray-drying protocol. The process involves two stages: the preparation of an emulsion and the generation of OED microparticles. Briefly, the macromolecule (e.g. human insulin) and other additives (stabilisers and/or surfactants) are dissolved in deionised water by adjusting the pH using diluted ammonia solution. The OEDs are dissolved in an organic solvent (ethyl acetate). The aqueous phase is then emulsified (Silverson mixer) into the organic phase to form a w/o emulsion. The emulsion is spray-dried, e.g. on a Buchi Mini 191 spray dryer, and particles are collected from both the cyclone and collection jar.

Another procedure is hydrophobic ion-pairing (HIP), using surfactants. This is a process which neutralises the charge on macromolecules such as proteins and renders them more hydrophobic in character. This enables proteins to dissolve in organic solvents, thus making them compatible with hydrophobic matrices. The aim of the process is to produce stable particles for sustained delivery of insulin via the lung.

Briefly, the process involves the precipitation of, say, insulin from dilute aqueous solution by combination with an equal weight ratio of a phospholipid surfactant, e.g. dipalmitoylphosphatidylglycerol (DPPG) or dipalmitoylphosphatidic acid (DPPA). For example, the precipitate is then dissolved in an organic solvent (DCM/ethanol; butanone) containing the OED. Microparticles are produced by spray-drying.

Different dosing schemes can also be achieved by the delivery system formulated. The delivery system can permit a quick release or flooding dose of the incorporated substance after administration, upon the dissolving and release of the substance from the delivery system. Coformulations of vehicles with slowly water-soluble glasses and plastics such as phosphate, nitrate or carboxylate glasses and lactide/glycolide, glucuronide or polyhydroxybutyrate plastics and polyesters, provide more slowly dissolving vehicles for a slower release and prolonged dosing effect. Optionally, a substance can be incorporated into the matrix which retards recrystallisation of the matrix, such as polyvinylpyrrolidone, or a hydrophobic substance can be incorporated in the matrix, so as to modify the release rate of the substance, such as a water insoluble wax or a fatty acid. See WO-A-93/10758.

The delivery systems can also be coformulated with a hydrophobically derivatised carbohydrate (HDC) glass forming material. HDC glass forming materials are described in WO-A-96/03978. As used herein, HDC refers to a wide variety of hydrophobically derivatised carbohydrates where at least one hydroxyl group is substituted with a hydrophobic moiety. Examples of suitable HDCs and their syntheses are described in Developments in Food Carbohydrate, 2 ed. C. K. Lee, Applied Science Publishers, London (1980). Other syntheses are described for instance, in Akoh et al. (1987), *J. Food Sci.* 52:1570; Khan et al. (1993) *Tet. Lett* 34:7767; Khan (1984) *Pure & Appl. Chem.* 56:833-844; and Khan et al. (1990) *Carb. Res.* 198:275-283.

The delivery of more than one bioactive material can also be achieved using a delivery system including multiple coatings or layers loaded with different materials or mixtures thereof administration of the solid dose delivery systems of the present invention can be used in conjunction with other conventional therapies and coadministered with other therapeutic, prophylactic or diagnostic substances. Compositions such as these are encompassed by this invention.

The solid delivery systems can be used to deliver therapeutic agents by any means including, but not limited to, topical, transdermal, ballistic, transmucosal, oral, gastrointestinal, intraperitoneal, subcutaneous, ocular, intramuscular, intravenous and by-inhalation (naso-pharyngeal and pulmonary, including transbronchial and transalveolar).

Topical administration is, for instance, by a dressing or bandage having dispersed therein a delivery system, or by direct administration of a delivery system into incisions or open wounds. Creams or ointments having dispersed therein slow release bead or microspheres of a delivery system are suitable for use as topical ointments or wound filling agents.

Compositions for transdermal administration are preferably powders of delivery systems in the form of preferably homogeneously sized microneedles or microbeads. Larger, macroscopic needle and bead forms of the delivery systems are also provided for subdermal implantation and extended drug delivery. The particle sizes should be small enough so that they cause only minimal skin damage upon administration. The powders can be prepackaged in single-dose, sealed, sterile formats. Suitable methods of transdermal administration include, but are not limited to, direct impact ballistic, trocar and liquid jet delivery.

The delivery systems suitable for transmucosal delivery include, but are not limited to, mucoadhesive wafers, films or powders, lozenges for oral delivery, pessaries, and rings and other devices for vaginal or cervical delivery.

Compositions suitable for gastrointestinal administration include, but are not limited to, pharmaceutically acceptable powders, tablets, capsules and pills for ingestion and suppositories for rectal administration.

Compositions suitable for subcutaneous administration include, but are not limited to, various implants. Preferably the implants are macroscopic discoid, spherical or cylindrical shapes for ease of insertion and can be either fast or slow release. Since the entire implant is dissolved in the body fluids, removal of the implant is not necessary. Furthermore, the implants do not contain synthetic polymers and are biodegradable.

Compositions suitable for ocular administration include, but are not limited to, microsphere and macrosphere formulations and saline drops, creams and ointments containing these and round-ended shaped rods which fit comfortably in the lower conjunctival fomix beneath the lower eyelid.

Compositions suitable for by-inhalation administration include, but are not limited to, powder forms of the delivery systems. There are a variety of devices suitable for use in by-inhalation delivery of powders. See, e.g. Lindberg (1993). Summary of Lecture at Management Forum 6-7 December 1993 "Creating the Future for Portable Inhalers". Additional devices suitable for use herein include, but are not limited to, those described in WO-A-94/13271, WO-A-94/08552, WO-A-93/09832 and U.S. Pat. No. 5,239,993.

The delivery systems are preferably biodegradable and release substances incorporated therein over a desired time period, depending on the particular application, and the composition of the system. As used herein, the term "biodegradable" refers to the ability to degrade under the appropriate conditions of use, such as outdoors, or in the body, for example by dissolution, devitrification, hydrolysis or enzymatic reaction.

Substances which can be incorporated into the delivery systems include, but are not limited to, medicinal or agricultural bioactive materials suitable for use in vivo and in vitro. Suitable bioactive materials include, but are not limited to, pharmaceutical agents, therapeutic and prophylactic agents, and agrochemicals such as pesticides and pheromones.

Suitable therapeutic and prophylactic agents include, but are not limited to, any therapeutically effective biological modifier. Such modifiers include, but are not limited to, pharmaceutical actives, subcellular compositions, cells, bacteria, viruses and molecules including, but not limited to, lipids, organics, proteins and peptides (synthetic and natural); peptide mimetics, hormones (peptide, steroid and corticosteroid), D and L amino acid polymers, saccharides including oligosaccharides and polysaccharides, nucleotides, oligonucleotides and nucleic acids, including DNA and RNA, protein-nucleic acid hybrids, small molecules and physiologically active analogs thereof. Further, the modifiers can be derived from natural sources or made by recombinant or synthetic means and include analogs, agonists and homologs.

As used herein "protein" refers also to peptides and polypeptides. Such proteins include, but are not limited to, enzymes, biopharmaceuticals, growth hormones, growth factors, insulin, monoclonal antibodies, interferons, interleukins and cytokines.

Organic compounds include, but are not limited to, pharmaceutically active chemicals. For instance, representative organic compounds include, but are not limited to, vitamins, neurotransmitters, antimicrobials, antihistamines, analgesics, β-agonists, β-antagonists, β-blockers, corticosteroids, and immunosuppressants.

Compositions comprising solid dose delivery systems containing prophylactic bioactive materials and carriers therefore are further encompassed by the invention. Preferable compositions include immunogens such as for use in vaccines. Preferably, the compositions contain an amount of the immunogen effective for either immunization or booster inoculation.

The following Examples illustrate the invention.

EXAMPLE 1

Ditrityl Trehalose

Trehalose dihydrate is briefly ground with a mortar and pestle before being dried at 2 millibar and 75° C. for twelve hours. The expected weight loss is 9.5%. The material is checked by adding 1 g to 7 ml pyridine with stirring. This rapidly gives a clear solution.

Anhydrous amorphous trehalose (100 g, $2.92 \times 10^{-1}$ mol) is dissolved in pyridine (400 ml) and trityl chloride (170 g, $6.10 \times 10^{-1}$ mol) is added slowly and the solution stirred at 40° C. for 24-36 hr, when tlc (4:1:1 EtOAc:MeOH:water) showed the reaction to be complete. Most of the pyridine is then removed under reduced pressure before the resulting syrup is poured into water (1 l) with stirring. The pale orange precipitate is collected by filtration, thoroughly washed with water (500 ml) and then dried under reduced pressure (10-15 mm Hg) at 70° C. Hot methanol (500 ml, 60° C.) is added to the solid and the slurry stirred for 5 min and filtered to collect the product. The solution contains mostly side products. Tlc (4:1:1 EtOAc:MeOH:water) shows the product as a spot moving near the solvent front (Rf~0.8). Small traces of lower running impurities are also seen. The product is then dried under vacuum (~2 mm Hg) at 70° C. for 12 hr. Crude yield of 6:6'-ditrityl trehalose is 157-181 g (65-75%). The crude product is sufficiently pure to be used in the next step.

Ditrityl Hexaacetyl Trehalose

Ditrityl trehalose (50 g, $6.05 \times 10^{-2}$ mol) is dissolved in pyridine (150 ml) and acetic anhydride (50 ml, $5.30 \times 10^{-1}$ mol) is added slowly with stirring and cooling so that the temperature is kept below 40° C. The solution is stirred for 4 hr at room temperature at which time tlc (1:1 EtOAc:light petrol) shows the reaction to be complete. Water (20 ml) is then added and the solution stirred for 30 min to hydrolyse excess acetic anhydride. Approximately half of the solvent is then removed under reduced pressure giving a yellow syrup. This is then poured into water (1 l) with vigorous stirring, giving a pale yellow precipitate which is collected by filtration and washed with water (500 ml). The product is then stirred with hot methanol (250 ml) for 10 min, collected and dried at room temperature overnight; Tlc (1:1 EtOAc:light petrol) shows a high running spot (Rf~0.7) with traces of two lower running compounds, monotriylheptaacetyltrehalose and octaacetyltrehalose. The crude yield of 6:6'-ditrityl-2,3,4:2',3',4'-hexaacetyl trehalose is 53.4 g, 82%. This material should be 95%+ pure (by tlc and nmr) to obtain good yields in the following steps.

mp 241-3° C.; $\alpha_D$+115° (CHCl$_3$); δ(CDCl$_3$) 7.18-7.43 (m, 3Ph), 5.48 (d, H-1,1'), 5.19 (dd, H-2,2'), 5.45 (t, H-3,3'), 5.15 (t, H-4,4'), 4.12 (m, H-5,5'), 3.10 (m, 2H-6,6'), 1.99 (s, 2CH$_3$), 1.89 (s, 2CH$_3$), 1.75 (s, 2CH$_3$).

Hexaacetyl Trehalose—Method 1

6:6'-Ditritylhexaacetyltrehalose (50 g, $4.63 \times 10^{-2}$ mol) is dissolved in glacial acetic acid (320 ml) by heating to 80° C. The solution is cooled in an ice bath to 15° C., before 45% w/v HBr in acetic acid (20 ml) is added dropwise with vigorous stirring over a period of 15 min, maintaining the temperature at 10-15° C. The mixture is immediately poured into cold water (350 ml) and stirred vigorously for 1 min. The precipitate of tritanol is collected by filtration and washed with a little water. The resulting solution is extracted with dichloromethane (2×150 ml) and washed with potassium carbonate solution (2×50 ml) and water (50 ml). Care must be taken to neutralise the solution and remove excess base. The extraction and washing should be done as quickly as possible to prevent decomposition. The product is stable in dry, neutral dichloromethane solution. It is dried over magnesium sulphate, most of the solvent being removed. The resulting syrup is crystallised at room temperature by the addition of methyl t-butyl ether (100 ml) to give 2,3,4:2',3',4'-hexaacetyl trehalose (19.3-20.6 g, 70-75%) as a white solid after drying at 30° C., 2 mmHg for 4 hr. Tlc (EtOAc) shows a single spot Rf~0.5. Impurities can be removed by repeated recrystallisation from CHCl$_3$/ether or ethanol/light petrol.

mp 92-5° C.; $\alpha_D$ +158° (CHCl$_3$); δ(CDCl$_3$) 5.31 (d, H-1,1'), 4.98 (dd, H-2,2'), 5.55 (t, H-3,3'), 5.02 (t, H-4,4'), 3.88 (m, H-5,5'), 3.55 (m, 2H-6,6'), 2.04 (s, 2CH$_3$), 2.02 (s, 2CH$_3$), 1.99 (s, 2CH$_3$).

Hexaacetyl Trehalose—Method 2

Ditrityl hexaacetyl trehalose (50 g, 46.4 mmol) is dissolved in acetonitrile (120 ml) and heated to 60° C. Amberlite IR-120 acidic resin (50 g), which had been washed with water (2×50 ml) to remove colour, is added and the mixture stirred for 2 hr. At this time tlc (2:1 EtOAc:petrol) shows the reaction to be complete.

The mixture is filtered while hot to recover the resin, and then allowed to cool to room temperature. Tritanol crystallises as a pale yellow solid from the solution and is collected by filtration. The remaining solution is evaporated under reduced pressure to give a yellow slurry. This is dissolved in MTBE (100 ml) with warming. The white solid which forms on cooling is collected and dried to give hexaacetyl trehalose (24.2 g, 88%) as a white powder.

Di-(β-Tetraacetyl Glucuronyl) Hexaacetyl Trehalose

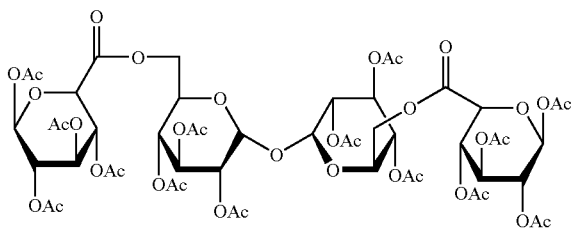

β-Tetraacetylglucuronic acid (51.0 g, 0.141 mol), hexaacetyl trehalose (40.0 g, 67.3 mmol) and DMAP (0.17 g, 1.41 mmol) are dissolved in acetonitrile (300 ml). Dicyclohexyl carbodiimide (32.0 g, 0.155 mol) is dissolved in acetonitrile (100 ml) and added dropwise over 15 min to the reaction mixture with stirring. A white precipitate quickly formed and the mixture becomes warm. After 2.5 hr, tlc (3:1 EtOAc:petrol) shows the reaction to be complete. The mixture is filtered to remove the precipitate of dicyclohexyl urea and the pale yellow solution evaporated under reduced pressure to give a white slurry. This is taken up in ethanol (150 ml) with heating and the solution allowed to cool. The resulting solid precipitate is collected, washed with ethanol (2×25 ml) and dried under vacuum at 40° C. The white powder is recrystallised by dissolving in hot ethyl acetate (150 ml) and adding ethanol (150 ml) to give di(β-tetraacetylglucuronyl)hexaacetyltrehalose (61.5 g, 71%) as a white powder.

Mp 156° C. (by DSC) δ (CDCl$_3$) 5.76 (2H, d, G-1), 5.46 (2H, t, T-3), 5.25 (6H, cms, T-1, G-3,4 ), 5.18 (2H, t, G-2), 5.02 (2H, dd, T-2), 4.92 (2H, t, T-4), 4.25 (2H, d, G-5), 4.14 (2H, d, T-6a), 4.06 (2H, dd, T-6b), 3.99 (2H, m, T-5), 2.08 (6H, s, 2×CH$_3$), 2.06 (6H, s, 2×CH$_3$), 2.01 (24H, 3s, 8×CH$_3$), 1.98 (6H, s, 2×CH$_3$) T=trehalose proton; G=glucuronyl proton Further characteristics of the compound of Example 1 are:

| | |
|---|---|
| molecular weight: | 1282 |
| glass temperature: | 110° C. |
| melt temperature: | 154° C. |
| log pow: | 2.9 |
| water solubility (glass): | 9.5 ppm |
| physical stability (t½ induction) at 40° C./75% RH: | >1176 h |
| hydrolytic stability (t½) at 20° C., pH 4: | 12 h |
| hydrolytic stability (t½) at 20° C., pH 7: | 14 h |
| hydrolytic stability (t½) at 20° C., pH 9: | <1 h |
| Hansen solubility polarity: | 11.1 |
| Hansen solubility H bonding: | 9.3 |
| Hansen solubility dispersion: | 15.5 |

EXAMPLE 2

4,6:4',6'-Dibenzylidene Trehalose

Anhydrous amorphous trehalose (200 g, 0585 mol) is added with vigorous stirring to a mixture of benzaldehyde (750 ml) and freshly ground zinc chloride (350 g). The mixture is stirred for 4-5 days at room temperature. Water (750 ml) and light petroleum (750 ml) are then added with stirring. The resulting white precipitate is collected, washed with water (250 ml) and light petroleum (250 ml) to give 4,6:4',6'-dibenzylidene trehalose (180-225 g, 60-84%) as a white solid. This is used without further purification.

Mp 196-99° C. δ (CD$_3$OD) 7.48 (4H, cm, ArH), 7.32 (6H, cm, ArH), 5.55 (2H, s, PhCH), 5.11 (2H, d, H-1,1'), 4.21 (2H, dd, H-6a,6a'), 4.10 (2H, dt, H-5,5'), 4.02 (2H, t, H-4,4'), 3.71 (2H, t, H-6b,6b'), 3.62 (2H, dd, H-2,2'), 3.47 (2H, t, H-3,3')

4,6:4',6'-Dibenzylidene-2,3:2',3'-Tetraisobutyroyl Trehalose

Dibenzylidene trehalose (100 g, 0.192 mol) is dissolved with stirring in pyridine (200 ml) and cooled in water. Isobutyroyl chloride (100 ml, 101.7 g, 0.954 mol) is then added dropwise over 15 min. so that the temperature of the reaction is kept at 40-50° C. The resulting yellow slurry is stirred for 2-3 hr at room temperature when tlc (2:3, EtOAc: light petrol) shows the reaction to be complete. 0.5M Hydrochloric acid (800 ml) is added and the mixture stirred for 30 min. The resulting solid is collected, washed with water (200 ml) and left to dry. Recrystallisation from MTBE (400 ml) and light petrol (500 ml) gives 4,6:4',6'-dibenzylidene-2,3:2',3'-tetraisobutyroyl trehalose (110.9 g, 72%) as a colourless crystalline solid.

Mp 179-182° C. δ (CDCl$_3$) 7.38 (10H, m, ArH), 5.48 (2H, s, PhCH), 5.63 (2H, t, H-3), 5.38 (2H,d, H-1), 5.02 (2H, dd, H-2), 4.20 (2H, dd, H-6a), 3.92 (2H, m, H5), 3.65 (4H, m, H-6b, 4), 2.65 (2H, m, CH), 2.57 (2H, m, CH), 1.14 (24H, m, CH$_3$)

2,3:2',3'-Tetraisobutyroyl Trehalose

Dibenzylidene tetraisobutyroyl trehalose (59 g, 73.7 mmol) is dissolved in acetonitrile (200 ml) and Amberlite IR-120 acid resin (50 g) is added with water (5 ml). The mixture is stirred and heated to reflux. After 1-1.5 hr tlc (2:1, EtOAc:light petrol) shows the reaction to be complete. The resin is filtered off and the solvent removed to give a colourless syrup. This is taken up in MTBE (50 ml) and light petrol (150 ml) is added with stirring giving a powdery precipitate. This is collected and dried to give 2,3:2',3'-tetraisobutyroyl trehalose (38.4 g, 84%) as a white powder.

Mp 228-230° C. δ (CDCl$_3$) 5.33 (2H, t, H-3), 5.23 (2H, d, H-1), 4.90 (2H, dd, H-2), 3.78 (6H, m, H-6a, 6b, 5), 3.68 (2H, t, H-4) 2.52(4H, m, CH), 1.14 (24H, m, CH$_3$)

6:6'-Di-(β-tetraacetyl glucuronyl)-2,3:2',3'-tetraisobutyroyl-4:4'-diacetyl trehalose 2,3:2',3'-Tetraisobutyroyltrehalose (40.0 g, 64.3 mmol), β-tetraacetylglucuronic acid (50.0 g, 0.138 mol) and DMAP (0.17 g, 1.38 mmol) are dissolved in acetonitrile (10 ml) and cooled to below 10° C. in ice water. Dicyclohexyl carbodiimide (28.5 g, 0.138 mol) in acetonitrile (60 ml) is then added dropwise with stirring over 10 min. A white precipitate forms. After 2 hr, tlc (3:2 ethyl acetate:petrol) shows the reaction to be complete. The mixture was filtered and the solvent removed to give a pale yellow syrup.

This syrup is dissolved in acetic anhydride (75 ml) and conc. sulphuric acid (5 drops) added. The solution becomes warm. After 2 hr this is poured into water (500 ml) and the mixture stirred for 30-40 min giving a powdery white precipitate. Crystallisation from methanol (300 ml) gives 6:6'-di-(β-tetraacetyl glucuronyl)-2,3:2',3'-tetraisobutyroyl-diacetyl trehalose (76.7 g, 85%) as a white powder.

δ (CDCl$_3$) 5.76 (2H, d, G-1), 5.50 (2H, t, T-3), 5.33 (2H, d, T-1), 5.26 (4H, m, G-3,4), 5.18 (2H, t, G-2), 4.98 (2H, dd,

T-2), 4.96 (2H, t, T-4), 4.24 (2H, d, G-5), 4.09 (2H, d, T-6a), 4.01 (2H, dd, T-6b), 3.86 (2H, m, T-5), 2.54 (2H, sept., CH), 2.48 (2H, sept., CH), 2.08 (6H, s, 2×CH$_3$), 2.00 (6H, s, 2×CH$_3$), 1.99 (24H, 3s, 8×CH$_3$), 1.97 (6H, s, 2×CH$_3$), 1.95 (6H, s, 2×CH$_3$), 1.14 (6H s, 2×CH$_3$), 1.13 (6H, s, 2×CH$_3$), 1.10, 1.09, 1.08, 1.07 (4×3H, 4s, 4×CH$_3$)

EXAMPLE 3

This Example illustrates a formulation of the invention, using cyclosporin as a model lipophile. A formulation comprising cyclosporin and the OED compound of Example 1 was prepared from a dicloromethane solution containing cyclosporin (20% +/–OED (80%) using a Buchi 191 Mini laboratory Spray Dryer. The product was initially assessed for surface morphology, particle size, particle size distribution, dispersion and in vitro release into selected aqueous media.

Volume particle size and distribution measured using an Aerosizer with Aerodisperser (API Aerosizer, Amherst Process Instrument Inc., USA) (shear force: peak, de-agglomeration: high, feed rate: low pin vibration: on and running time 180 seconds) showed that the formulation had a particle size of less than 3 μm, with the majority of particles having a distribution between 1 to 2 μm. Glass transition was detected using a differential scanning calorimeter (Perkin Elmer DSC 7, 0-200° C. at 10° C./minute) and no crystalline peaks were detected by XRPD (Siemens D5000 diffractometer with CuKα radiation).

Dispersion of the formulation when delivered from an Inveresk Dry Powder Delivery System (Inveresk Research, UK) was assessed using a 5-stage liquid impinger (Copley Instrument Ltd., UK) at a flow rate of 60 L/minutes and duration of 4 seconds. The results showed that over 50% of the loaded doses were delivered, of which over 50% presented as fine particles (Fine particle dose was defined as the dose deposited at stages 3, 4 and 5). In vitro release of cyclosporin from the formulations was evaluated using a Distek dissolution apparatus (Distek Model 2100B, USA, dissolution media: 900 ml DI water and 0.05% tween 80 solution, paddle speed: 100 rpm, temperature: 37° C.).

The in vivo behaviour was investigated by randomly administering formulations equivalent to approximately 10 mg cyclosporin into the dog lung (male Beagle dog. Weight: ~10 kg) via a surgically prepared tracheostome. Blood samples were taken before and after dosing and measured for cyclosporin whole blood level using a microparticle enzymatic immunoassay (MEIA, Abbott Diagnostics, USA).

In vitro performance of cyclosporin/OED formulation

| Formulation | Tg (° C.) | ΔCp (J/g ° C.) | Particle size/distribution | | | Delivery and Dispersion of the formulations | | |
|---|---|---|---|---|---|---|---|---|
| | | | P10 (μm) | P50 (μm) | P90 (μm) | LD (mg) | ED (mg) | FD (mg) |
| Cyclosporin | — | — | 0.83 | 1.25 | 2.36 | 10 | 5 | 3.6 |
| Cyclosporin/OED (20/80) | 106.5 | 0.392 | 1.06 | 1.49 | 2.18 | 10 | 5.2 | 3.7 |

LD: Loaded dose
ED: Emitted dose
FD: Fine particle dose

EXAMPLE 4

Formulations of insulin (5, 10 or 20%) and the OED compound of Example 1 with 1% DPPG was prepared by the single emulsion spray-drying protocol described above. No evidence of morphological changes was observed on storage for 1 month at 25° C./60% RH and 40° C./75% RH.

For in vitro release studies, samples equivalent to 5 mg insulin were suspended in 100 ml PBS, pH 6.4, in 200 ml containers kept in a 37° C. oven. The medium was continuously stirred using a magnetic stirrer (350 rpm). Samples were taken at selected times and assayed using HPLC. Increased insulin concentration gave more rapid release.

EXAMPLE 5

Formulations were prepared by the HIP protocol described above. All of these batches contain 74% OED, 13% insulin and 13% DPPG/DPPA, except for a single batch where the insulin load was reduced to 3%. The physical characteristics of these particles have been determined. The T$_g$s of the particles reflect those of the constituent OEDs. The aerodynamic size (~3 μm), the absence of aggregation, the spherical morphology, and the low polydispersity of the particles indicate that the formulations are suitable for pulmonary delivery. This is confirmed by dispersibility studies on an Anderson Cascade Impactor which yields a fine particle fraction of around 40%.

Scheme 1

-continued
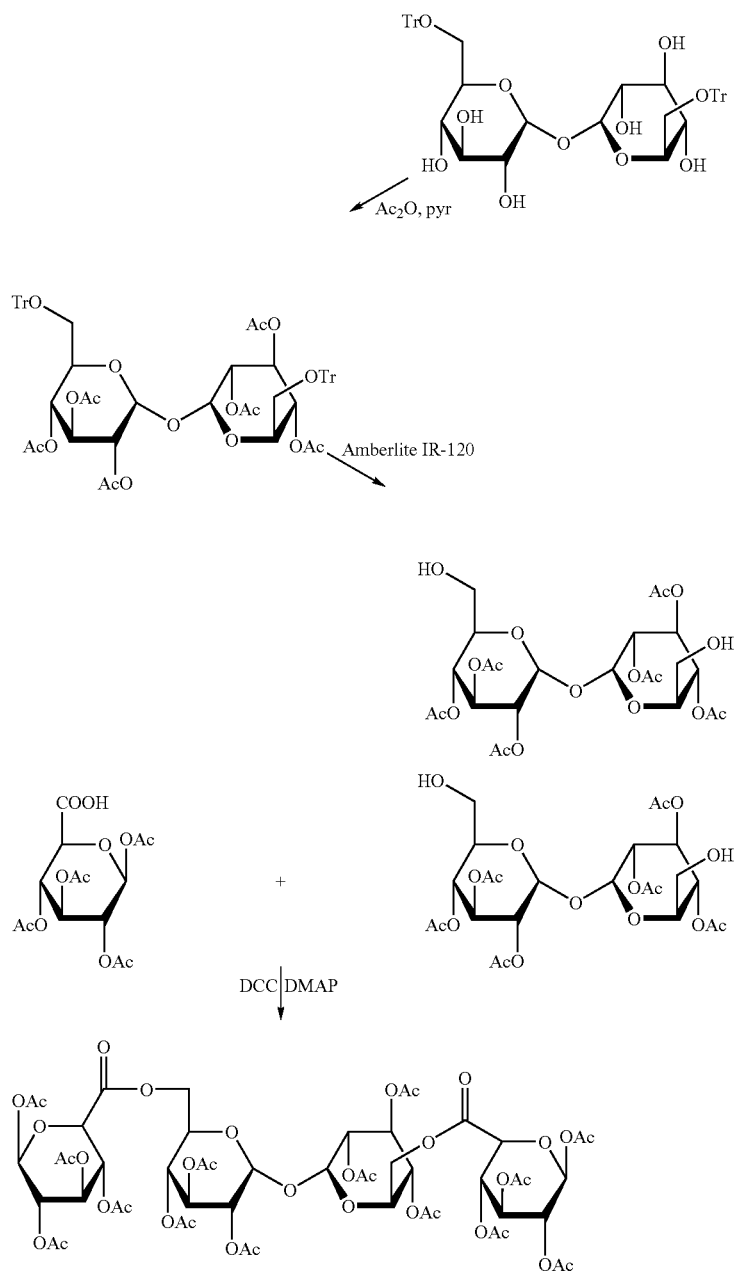
Scheme 2
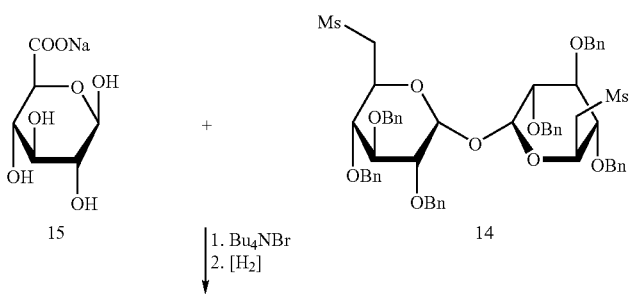

-continued

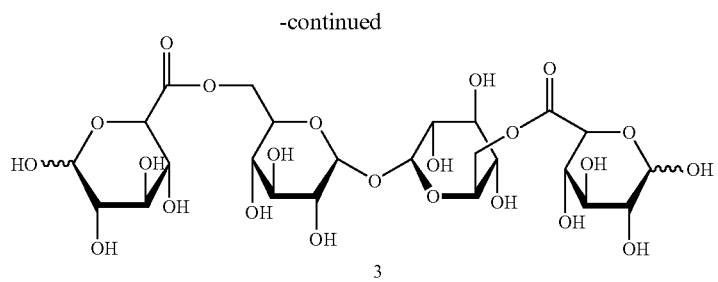

3

Scheme 3

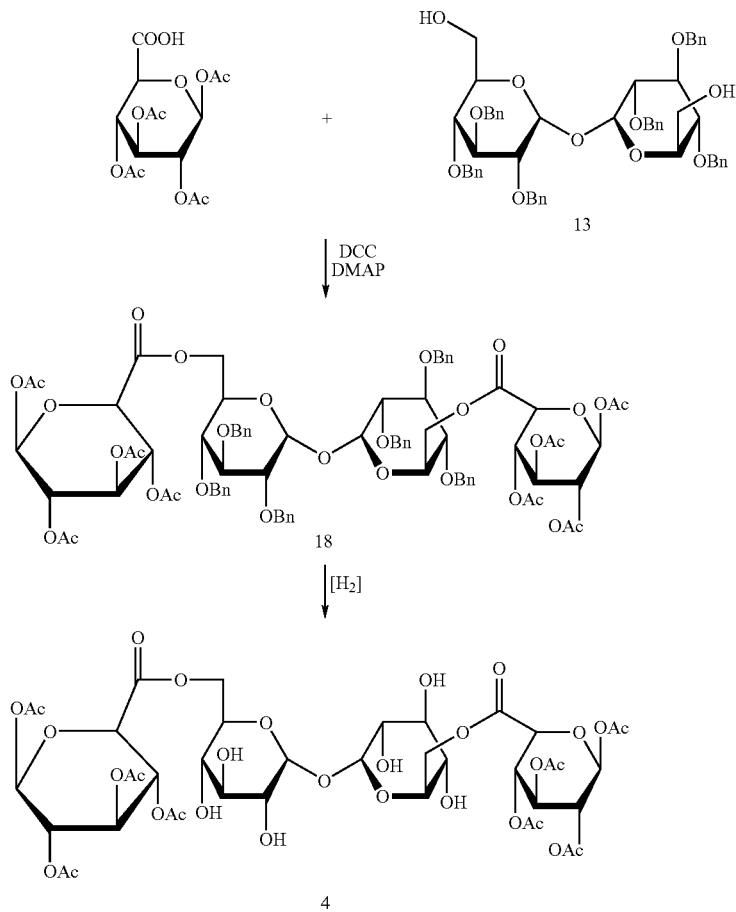

The invention claimed is:

1. A composition comprising a therapeutic agent selected from insulin and cyclosporin and a compound which is di(β-tetraacetyl-glucuronyl)hexaacetyltrehalose or 6:6'-di(β-tetraacetyl-glucuronyl)-2,3:2',3'-tetraisobutyroyl-4:4'-diacetyltrehalose.

2. A compound which is di(β-tetraacetyl-glucuronyl)-hexaacetyltrehalose or 6:6'-di(β-tetraacetyl-glucuronyl)-2,3:2',3'-tetraisobutyroyl-4:4'-diacetyltrehalose.

3. The compound according to claim 2, which is di(β-tetraacetyl-glucuronyl)-hexaacetyltrehalose.

4. The compound according to claim 2, which is 6:6'-di(β-tetraacetyl-glucuronyl)-2,3:2',3'-tetraisobutyroyl-4:4'-diacetyltrehalose.

5. The composition according to claim 1, which is in the form of a solid solution.

6. The composition according to claim 1, which is in the form of needles, microneedles, microfibres or particles.

7. The composition, according to claim 1, wherein the compound is di(β-tetraacetyl-glucuronyl)-hexaacetyltrehalose.

8. The composition, according to claim 1, wherein the compound is 6:6'-di(β-tetraacetyl-glucuronyl)-2,3:2',3'-tetraisobutyroyl-4:4'-diacetyltrehalose.

* * * * *